United States Patent [19]
Sawada et al.

[11] 4,302,964
[45] Dec. 1, 1981

[54] KNOCK SENSOR

[75] Inventors: Daisaku Sawada, Susono; Juhei Takahashi; Kenzo Miura, both of Yokohama, all of Japan

[73] Assignees: Matsushita Electric Industrial Co., Ltd., Osaka; Toyota Jidosha Kogyo Kabushiki Kaisha, Toyota, both of Japan

[21] Appl. No.: 112,136

[22] Filed: Jan. 14, 1980

[30] Foreign Application Priority Data

Jan. 29, 1979 [JP] Japan .................................. 54/9505

[51] Int. Cl.³ .................... G01L 23/22; G01N 15/00
[52] U.S. Cl. ........................................ 73/35; 73/651
[58] Field of Search ............... 73/35, 654, 517 R, 651; 310/329, 330, 332, 354

[56] References Cited
U.S. PATENT DOCUMENTS

| | | | |
|---|---|---|---|
| 2,045,403 | 6/1936 | Nicholides | 310/329 X |
| 2,964,939 | 12/1960 | Forrest | 73/35 |
| 3,113,223 | 12/1963 | Smith et al. | 310/329 |
| 3,453,457 | 7/1969 | Hayer et al. | 310/329 X |
| 4,096,735 | 6/1978 | Huntzinger et al. | 73/35 |
| 4,111,035 | 9/1978 | West et al. | 73/35 |

*Primary Examiner*—James J. Gill
*Attorney, Agent, or Firm*—Stevens, Davis, Miller & Mosher

[57] ABSTRACT

A knock sensor includes a metal case of a shape that can be easily mounted to an engine, a base of a size that can be fitted in the case and having preliminarily mounted thereon a knock detecting ceramic vibrator, and a cover adapted to be fitted in the case so as to hold the base in place when fitted in the case.

2 Claims, 12 Drawing Figures

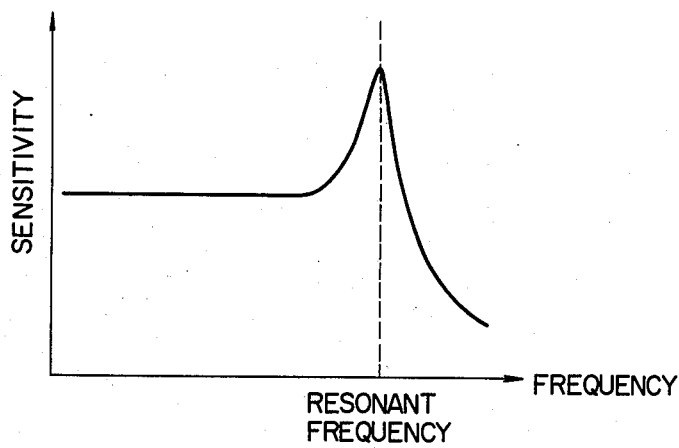
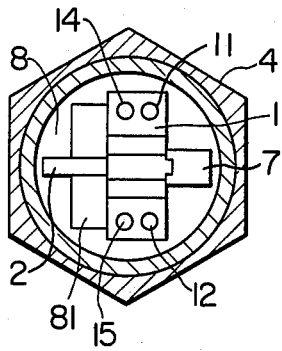
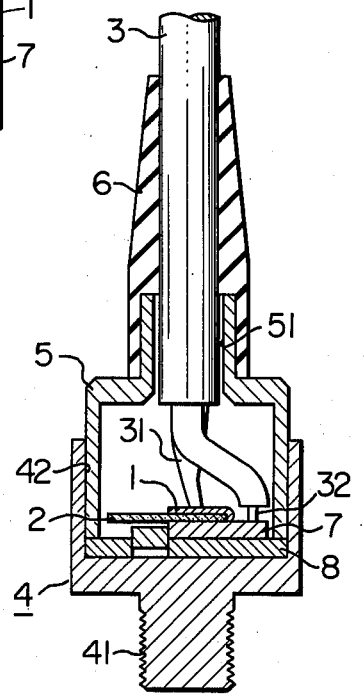
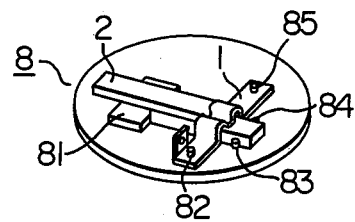
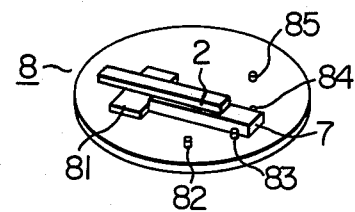
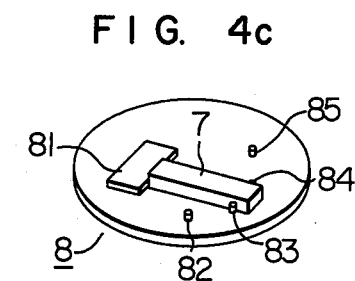
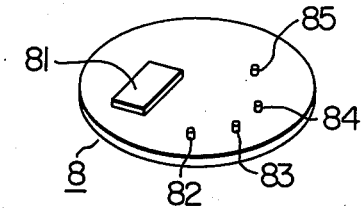

4,302,964

KNOCK SENSOR

BACKGROUND OF THE INVENTION

This invention relates to a knock sensor for detecting knocking of an engine for automotive vehicles.

Knocking of an automotive vehicle is considered to be a factor which is detrimental to the smooth running of the vehicle, the durability of the engine and the improvement of fuel consumption. As regards the measures taken to counter knock, it is known in the art that the knock can be readily eliminated by controlling the ignition timing, the air-fuel mixture ratio or the like. The known knock sensors are generally so designed that the knock condition is detected from the peak of a spectrum generated as a vibration waveform of the engine of a vehicle and the frequency of the peak which varies in dependence on the type and size of engines is in the range of 6 to 9 kHz. Since variation in the spectrum is picked up in the vicinity of the vehicle engine where the S/N ratio is extremely inferior electrically, the sensitivity-frequency characteristics of the knock sensor for vibrations should preferably be such that the resonant frequency corresponding to the frequency of the peak has a high quality factor as shown in FIG. 1.

Also the knock sensor should preferably be so constructed that it can be mounted to an engine easily.

SUMMARY OF THE INVENTION

It is the object of this invention to provide a knock sensor which is easy to manufacture by virtue of the use of a knock detecting device employing a ceramic vibrator.

It is another object of the invention to provide such knock sensor which can be mounted to an engine easily.

BRIEF DESCRIPTION OF THE DRAWINGS

FIG. 1 is a knock sensor characteristic diagram.

FIGS. 2 and 3 are sectional views showing a knock sensor according to an embodiment of the invention.

FIGS. 4a to 4d are diagrams showing the manufacturing steps of a part of the sensor shown in FIGS. 2 and 3.

DESCRIPTION OF THE PREFERRED EMBODIMENTS

The present invention will now be described in greater detail with reference to the embodiment shown in FIGS. 2 to 7.

Figure 5A:
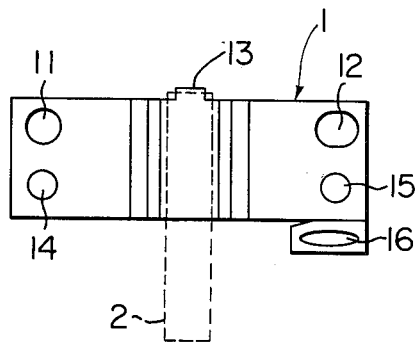
FIGS. 5a and 5b are respectively a plan view and front view of a component part of the sensor.
Figure 5B:
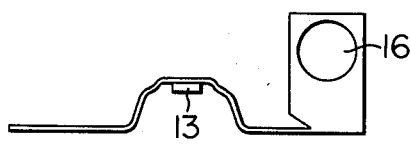

In the Figures, numeral 1 designates a keeper for a piezoelectric ceramic type vibrator 2 having a resonance frequency corresponding to the one shown in FIG. 1, and the keeper 1 includes, as shown in FIGS. 5a and 5b, guide holes 11 and 12, a positioning stopper 13, welded joints 14 and 15 and an opening 16 for guiding a sheath 31 of a sealed cable 3. Numeral 4 designates a metal case having an outer periphery formed into a multi-sided shape (e.g., the hexagon) and including a threaded portion 41 on the lower part thereof and an opening 42 for accommodating the vibrator 2, etc. Numeral 5 designates a cover including a hole 51 for receiving the sealed cable 3 and press fit in the opening 42 to close it, 6 a rubber bushing, 7 a supporting plate, and 8 a base of the size which can be received in the opening 42 and including a projection 81 positioned to contact one end of the supporting plate 7 and guide pieces 82 to 85 as shown in FIGS. 4a to 4d. In this case, the keeper 1 is made integral with the base 8 by assembling the supporting plate 7, the vibrator 2 and the keeper 1 in the sequence shown in FIGS. 4d, 4c, 4b, 4a, adjusting their positions and then spot welding at the positions 14 and 15.

More specifically, in the condition of FIG. 4c the position of the supporting plate 7 is determined by the projection 81 and the guide pieces 83 and 84 and the vibrator 2 is positioned on the supporting plate 7 as shown in FIG. 4b. Then the holes 11 and 12 in the keeper 1 are respectively aligned with the guide pieces 82 and 85 and the positioning of the vibrator 2 is accomplished by the positioning stopper 13.

Figure 6:
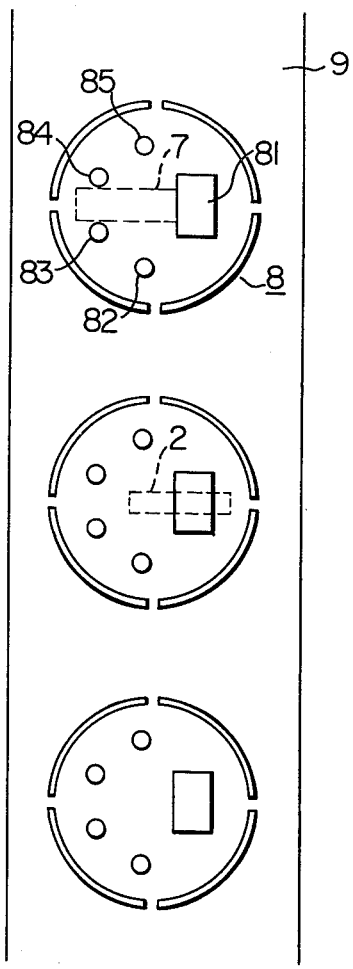
FIG. 6 shows diagrams indicating another manufacturing steps of the part of the sensor.

In this case, in view of the easiness of assembling of the vibrator 2, etc., it is possible to effect the positioning and assembling of the supporting plate 7, the vibrator 2 and the keeper 1 to the base 8 in the form of a plate material 9 pressed as shown in FIG. 6 (i.e., the base 8 which has not been separated as yet) by the same manufacturing steps as shown in FIGS. 4a and 4d and then separate the base 8 as an individual item. After the vibrator 2 and others have been assembled to the base 8 as shown in FIG. 4a, a core wire 32 of the sealed cable 3 which was inserted through the cover 5 is electrically connected to the supporting plate 7 and the sheath 31 is also electrically connected to the keeper 1. Then the cover 5 is press fit into the case 4 and the base 8 is placed by the cover 5 in position within the opening 42 of the case 4. The gap between the sealed cable 3 and the hole 51 in the cover 5 is hermetically sealed by means of the rubber bushing 6.

Figure 7:
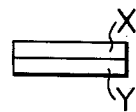
FIG. 7 is a sectional view showing the construction of the vibrator.

The vibrator 2 may be advantageously composed of two vibrator elements X and Y each having an electrode on each of the upper and lower surfaces and arranged one upon another as shown in FIG. 7.

The present invention has been described with reference to its preferred embodiment and the described manufacturing method is advantageous in that the need for adjustment of the resonance frequency of the vibrator 2 will be eliminated by selecting the projected length of the vibrator 2 to correspond to a desired frequency at the time that the keeper 1 is assembled to the base 8. Further the fact that the lower surface of the vibrator 2 is connected electrically to the supporting plate 7 has the effect of making easy the taking of an output from the vibrator 2 and the fact that the base 8 is held in place by the cover 5 has the effect of making the manufacture of knock sensor easy on the whole. Also the fact that the outer periphery of the case is formed into a multi-sided shape has the effect of making easy the mounting of the sensor to an engine.

Figure 8:
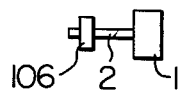
FIG. 8 is a plan view showing another form of the vibrator.

The vibration of the engine is applied through the case 4 to the vibrator 2 mounted inside the case 4 so that a change in the output due to the vibration of the vibrator 2 is taken out by way of the sealed cable 3, and an additional mass 106 may be attached to the vibrator 2 as shown in FIG. 8 so as to adjust the vibrator 2. Further, from the standpoint of manufacture, reliability and so on, it is possible to advantageously use iron material for the case 4 and the cover 5, stainless steel for the base 8 and the keeper 1 and good heat-resisting material for the sealed cable 3.

We claim:

1. A knock sensor comprising:
   a metal case having a multi-sided outer peripheral shape and including in a lower part thereof a projected portion adapted for fixedly fastening said case to an engine, said metal case having a vibrator receiving opening in an upper part thereof;
   a vibrator for detecting a knock of said engine, said vibrator being mounted on a supporting plate so that one end of said vibrator extends beyond a corresponding end of said supporting plate, a first surface of said vibrator and a surface of said supporting plate being electrically conductive and in contact with each other;
   a base having a size for being placed in said vibrator receiving opening, said base having on a surface thereof a projection and a guide means for respectively guiding and positioning said supporting plate and a vibrator keeper;
   said vibrator keeper pressing and securing the remaining end of said vibrator against said supporting plate and being in electrical contact with a second surface of said vibrator, said keeper being locked by said guide means; and
   a cover having a periphery of a size fitted to said vibrator receiving opening of said metal case and having a through hole at the center of said cover for receiving a sealed cable, said cable having a core and a sheath, one of which is connected to said supporting plate and the other of which is connected to said keeper, said cover being accommodated in said opening of said metal case whereby an edge of said cover securely locks said base in place.

2. A knock sensor according to claim 1, wherein said cover is press fitted into said vibrator receiving opening of said metal case.

* * * * *